(12) United States Patent
Lombardo

(10) Patent No.: US 11,547,399 B2
(45) Date of Patent: Jan. 10, 2023

(54) ARTICULATING SUTURE HOOK

(71) Applicant: Conmed Corporation, Utica, NY (US)

(72) Inventor: Giuseppe Lombardo, New Port Richey, FL (US)

(73) Assignee: Conmed Corporation, Utica, NY (US)

( * ) Notice: Subject to any disclaimer, the term of this patent is extended or adjusted under 35 U.S.C. 154(b) by 184 days.

(21) Appl. No.: 16/158,839

(22) Filed: Oct. 12, 2018

(65) Prior Publication Data

US 2019/0110788 A1   Apr. 18, 2019

Related U.S. Application Data

(60) Provisional application No. 62/572,671, filed on Oct. 16, 2017.

(51) Int. Cl.
*A61B 17/04* (2006.01)
*A61B 17/06* (2006.01)
*A61B 17/00* (2006.01)

(52) U.S. Cl.
CPC ...... *A61B 17/0469* (2013.01); *A61B 17/0482* (2013.01); *A61B 17/06109* (2013.01); *A61B 2017/00309* (2013.01); *A61B 2017/047* (2013.01); *A61B 2017/06052* (2013.01)

(58) Field of Classification Search
CPC .......... A61B 17/0469; A61B 17/06109; A61B 17/0482; A61B 2017/00309; A61B 2017/047
See application file for complete search history.

(56) References Cited

U.S. PATENT DOCUMENTS

| 8,142,464 | B2 * | 3/2012 | Mitusina | A61B 17/32002 |
| | | | | 606/180 |
| 9,226,747 | B2 * | 1/2016 | Oren | A61B 17/0483 |
| 2005/0216018 | A1 * | 9/2005 | Sennett | A61B 17/1671 |
| | | | | 606/79 |
| 2012/0277730 | A1 * | 11/2012 | Salahieh | A61M 25/0136 |
| | | | | 604/527 |
| 2013/0158567 | A1 * | 6/2013 | Levin | A61B 17/0401 |
| | | | | 606/144 |
| 2016/0022313 | A1 * | 1/2016 | Yoshida | A61B 17/3478 |
| | | | | 606/185 |

\* cited by examiner

*Primary Examiner* — Katherine H Schwiker
*Assistant Examiner* — Raihan R Khandker
(74) *Attorney, Agent, or Firm* — Bond, Schoeneck & King, PLLC; Frederick J. M. Price

(57) ABSTRACT

An articulating suture hook for passing or retrieving suture. The suture hook having a handle with a proximal end and distal end. A stiffening tube is fixed to the distal end of the handle extending distally from the handle. A flexible outer tube is fixed to the stiffening tube and extends distally therefrom. A cut portion of the flexible outer tube has a plurality of cuts positioned therealong. In a first configuration, the flexible outer tube extends parallel to or in alignment with the stiffening tube, but in a second configuration, the flexible outer tube is curved at the cut portion. The plurality of cuts may be arranged into two patterns. Each cut arranged in a first pattern is offset at an angle from each cut arranged in a second pattern. The pattern, shape, and size of the cuts determines the movement of the flexible outer tube to the second configuration.

14 Claims, 10 Drawing Sheets

ARTICULATING SUTURE HOOK

CROSS-REFERENCE TO RELATED APPLICATIONS

This application claims priority to U.S. Provisional Patent Application Ser. No. 62/572,671, filed on Oct. 16, 2017 and entitled "System and Method for Articulating Suture Hook," the entirety of which is incorporated herein by reference.

BACKGROUND OF THE INVENTION

1. Field of the Invention

The present disclosure is directed generally to a system and method for passing or retrieving suture with a needle tip and, more particularly, to a system and method for deforming a needle tip such that it is movable between a straight first configuration and a curved second configuration.

2. Description of Related Art

Suture hooks are commonly passed through portals or through soft tissue via an incision on the skin for arthroscopic procedures. For example, a suture hook may be passed through such portal or incision for bone repair procedures, including shoulder instability repair or rotator cuff repair. Common suture hooks have single curve or compound curve shapes. The curved shape is necessary to enable the surgeon to capture the appropriate soft tissue piece to fixate the tissue.

The act of using preformed curved suture hooks presents a challenge, especially in arthroscopic procedures, because the curvature of the suture hook requires a larger cannula. Additionally, the curved portion of the suture hook can catch on an undesired portion of soft tissue or damage the cannula seal during passage into the joint. Often, a surgeon will initially select a certain pre-curved hook only to discover that a different suture hook is needed. Alternatively, a surgeon may discover that the suture hook must be moved to another location once the suture hook is in the joint. Removal of the suture hook from the joint, in these situations and more, can cause damage to the cannula or the surrounding soft tissue, as described above.

Furthermore, the curved lumen of the suture hook is not desirable for passing the suture therethrough. A curved lumen with an acute bend can make it difficult to pass suture therethrough due to the increased friction created. Problems caused by suture hooks are frustrating to surgeons and increase the overall surgical procedure time.

Therefore, there is a need for a means of introducing a suture hook into the joint, which allows the user to select a smaller cannula and make a smaller incision, lessens the risk of getting caught in soft tissue, and provides the ability to adjust the curvature as needed to facilitate suture passage once in the joint.

SUMMARY OF THE INVENTION

Embodiments of the present invention are directed to an articulating suture hook. According to one aspect, the suture hook has a handle with a proximal end and distal end. A stiffening tube is fixed to the distal end of the handle and extends distally from the handle. A flexible outer tube is fixed to the stiffening tube and extends distally therefrom. A cut portion of the flexible outer tube has a plurality of cuts. In a first configuration, the flexible outer tube extends parallel to or in alignment with the stiffening tube, but in a second configuration, the flexible outer tube is curved at the cut portion.

According to another aspect, the suture hook has a cannulated handle with a proximal end and distal end. A cannulated stiffening tube is fixed to the distal end of the handle and extends distally from the handle. A flexible cannulated outer tube is fixed to the stiffening tube and extends distally therefrom. A flexible cannulated inner tube is slidably attached to the flexible cannulated outer tube and terminates in a distal tip. A cut portion of the flexible cannulated outer tube has a plurality of cuts. Of the plurality of cuts, there is a first set of cuts and a second set of cuts. The first set of cuts is arranged in a first pattern and the second set of cuts is arranged in a second pattern. The second pattern is different from the first pattern. In a first configuration, the flexible cannulated outer tube extends parallel to or in alignment with the stiffening tube. In a second configuration, the flexible cannulated outer tube is curved at the cut portion.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the invention will be apparent from and elucidated with reference to the embodiment(s) described hereinafter.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
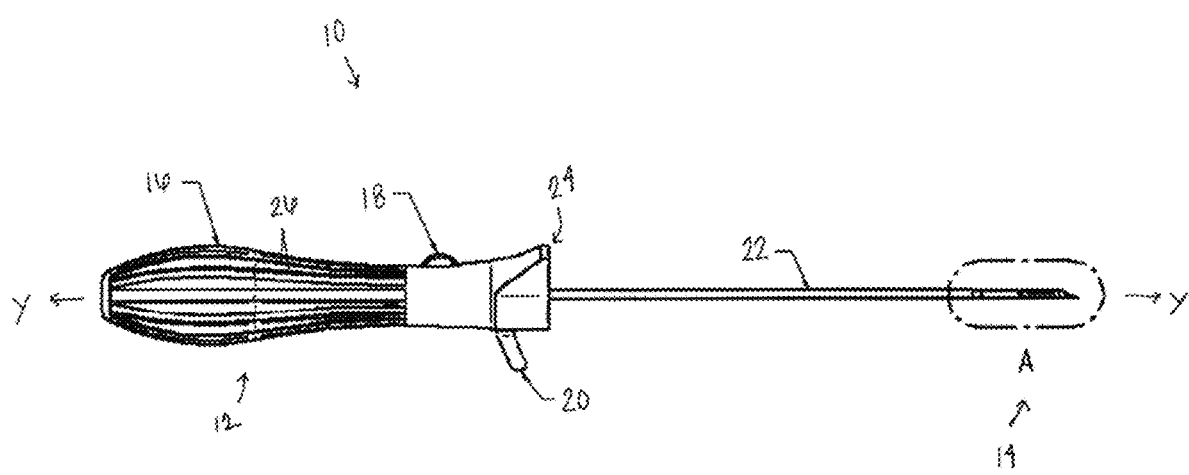
FIG. 1 is a side view schematic representation of an articulating suture hook in a first configuration, according to an embodiment.

Referring now to the figures, wherein like reference numerals refer to like parts throughout, FIG. 1 shows a side view schematic representation of an articulating suture hook 10 in a first configuration, according to an embodiment. In the depicted embodiment, the suture hook 10 extends along a central longitudinal y-y axis with a proximal end 12 and a distal end 14. The proximal end 12 of the suture hook 10 comprises a handle 16, which includes a suture advancing mechanism 18 and an actuator 20. In the depicted embodiment, the suture advancing mechanism 18 and the actuator 20 are on opposing sides of the handle 16; however, any suitable configuration and/or arrangement of the suture advancing mechanism 18 and actuator 20 along the handle 16 can be used (as should be understood by a person of ordinary skill in the art in conjunction with a review of this disclosure). As also shown in FIG. 1, a relatively inflexible stiffening tube 22 extends from the handle 16 to the distal end 14 of the suture hook 10. The stiffening tube 22 is cannulated and fixed to a distal end 24 of the handle 18.

In the depicted embodiment, the handle 16 has a changing diameter along the central longitudinal y-y axis. The changing diameter of the handle 16 creates an ergonomic design, which provides a better grip and more comfortable use of the suture hook 10. As also shown in FIG. 1, the handle 16 may also include one or more ridges, channels, or other grooves 26 along at least a portion of the length the handle 16 (extending approximately parallel to the central longitudinal y-y axis). The grooves 26 also provide a better gripping surface for the surgeon during use.

Figure 2:
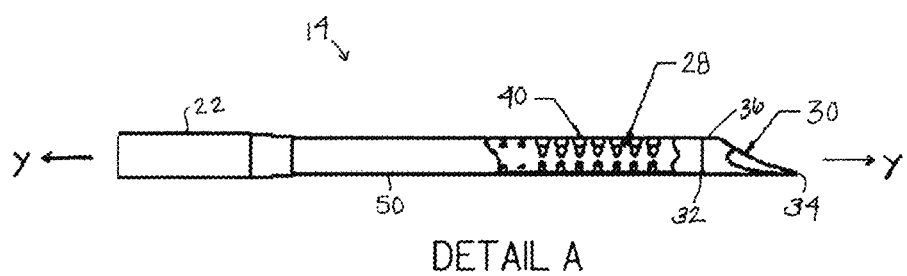
FIG. 2 is a close-up side view schematic representation of the distal end of the suture hook, according to an embodiment.
Figure 8:
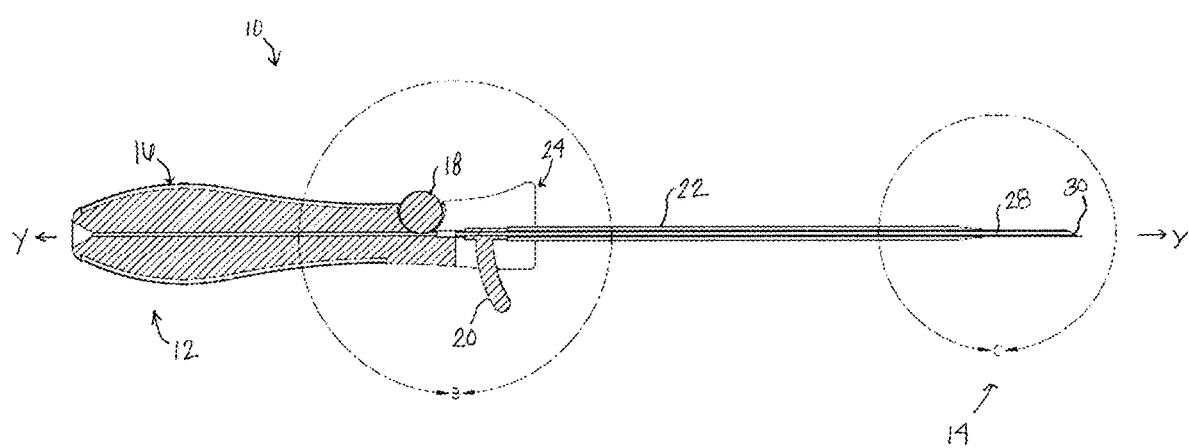
FIG. 8 is a side section view schematic representation of an articulating suture hook in a first configuration, according to an embodiment.
Figure 9:
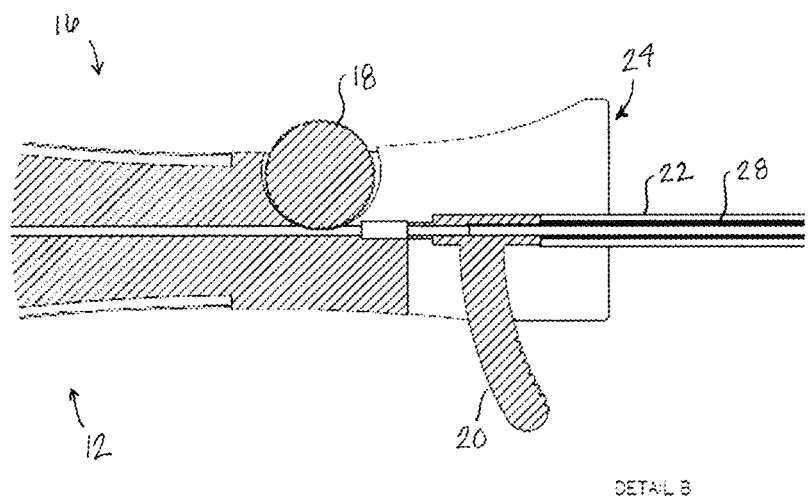
FIG. 9 is a close-up side section view schematic representation of the handle of the articulating suture hook of FIG. 8.
Figure 10:
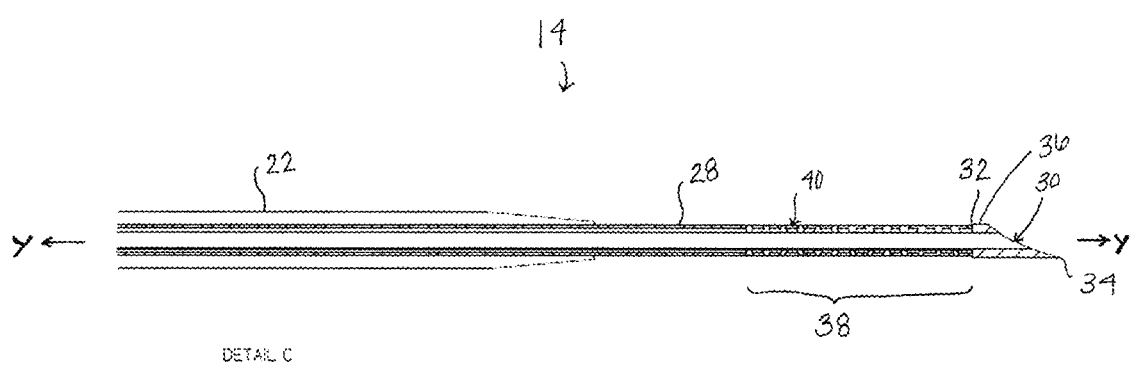
FIG. 10 is a close-up side section view schematic representation of the distal end of the articulating suture hook of FIG. 8.

Turning now to FIG. 2, there is shown a close-up side view schematic representation of the distal end 14 of the suture hook 10, according to an embodiment. Specifically, FIG. 2 shows a close-up view of Detail A in FIG. 1. As shown in FIG. 2, the distal end 14 of the suture hook 10 comprises an outer tube 28 extending from the stiffening tube 22 along the central longitudinal y-y axis. The outer tube 28 is flexible and cannulated. The flexible cannulated outer tube 28 is fixed to the stiffening tube 22 (also shown in FIGS. 8-9). The outer tube 28 extends distally to a flexible cannulated inner tube 30 and terminates at an end 32, as shown in the depicted embodiment. The inner tube 30 is positioned slidably within the outer tube 28 and extends distally to a distal tip 34 on the inner tube 30. The inner tube 30 is connected to the actuator 20 within the handle 16, as shown in FIGS. 8-9. The inner tube 30 is also attached to the end 32 of the outer tube 28. In one embodiment, the distal tip 34 is welded to the end 32 of the outer tube 28. Thus, in an embodiment, the inner tube 30 is slideable within the outer tube 28, but movement of the inner tube 30 within the outer tube 28 causes the outer tube 28 to deform. In the embodiment depicted in FIGS. 2 and 10, the distal tip 34 of the outer tube 28 has a shoulder 36 with a large diameter.

Figure 3:
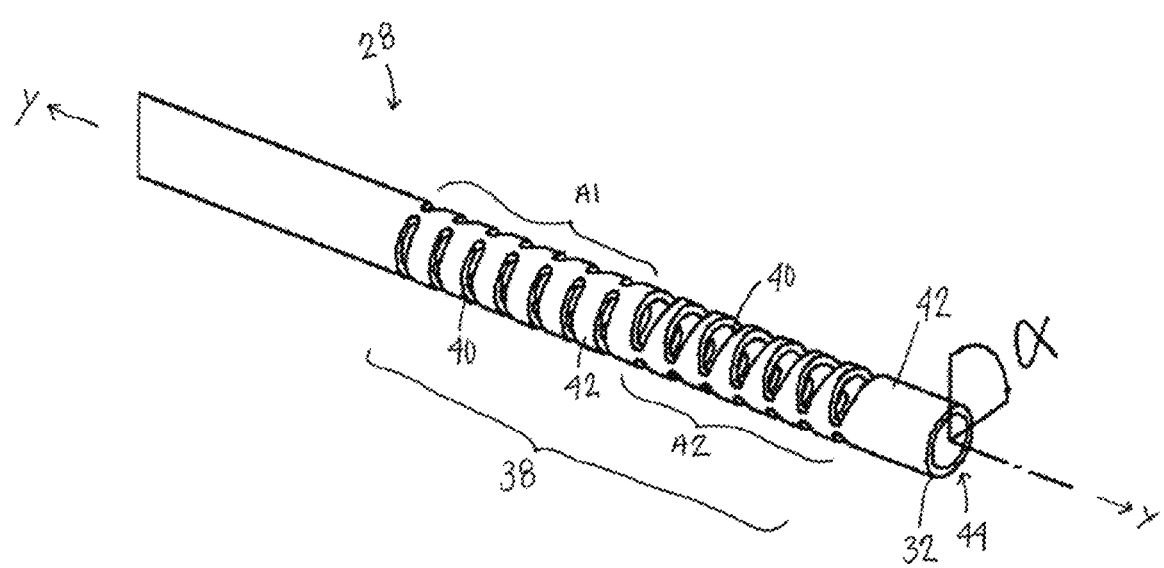
FIG. 3 is a top perspective view schematic representation of a cut portion of the flexible cannulated outer tube of the suture hook, according to an embodiment.

Referring briefly to FIG. 3, there is shown a top perspective view schematic representation of a cut portion 38 of the flexible cannulated outer tube 28 of the suture hook 10, according to an embodiment. In the depicted embodiment, outer tube 28 comprises a cut portion 38 having a plurality of cuts 40 (i.e., apertures or other openings) extending from an exterior surface 42 of the outer tube 28 through to an inner channel 44 of outer tube 28. The cuts 40 may comprise any pattern (i.e., configuration) or shape. The pattern and shape of the cuts 40 influence the shape, direction, and magnitude of the curvature of the suture hook 10. In the depicted embodiment, the cut portion 38 comprises a plurality of cuts 40 arranged in a first pattern A1 adjacent a plurality of cuts 40 arranged in a second pattern A2. The plurality of cuts 40 arranged in the second pattern A2 are offset by angle α from the plurality of cuts 40 arranged in the first pattern A1. In FIG. 3, the angle α is 90 degrees so that the planes of curvature are orthogonal to one another. The first and second patterns A1, A2 can be adjusted so the final shape of the suture hook 10 can be any number of complete revolutions if desired (as should be understood by a person of ordinary skill in the art in conjunction with a review of this disclosure).

Figure 4:
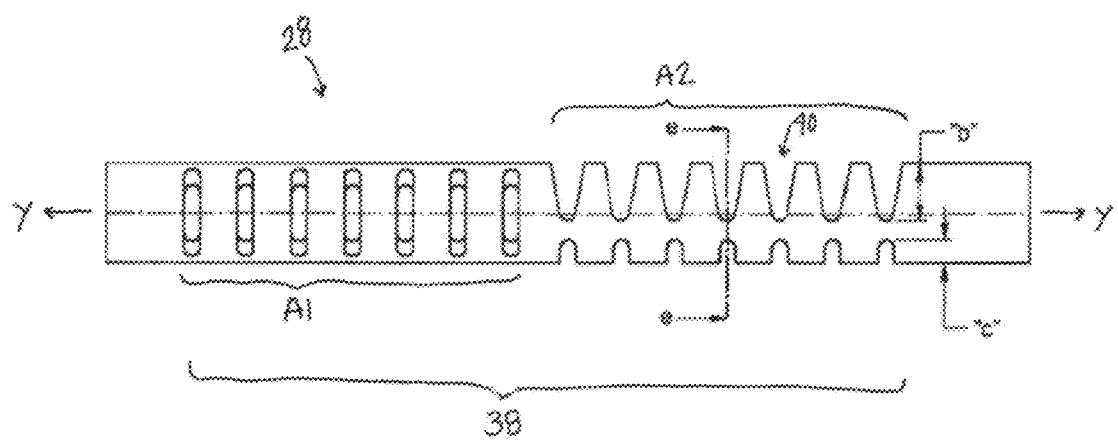
FIG. 4 is a detailed side view schematic representation of the cut portion of the suture hook, according to an embodiment.

Turning now to FIG. 4, there is shown a detailed side view schematic representation of the cut portion 38 of the suture hook 10, according to an embodiment. In the depicted embodiment, the direction of the curvature of the suture hook 10 is defined by the depth of the cuts 40 along the central longitudinal axis y-y. The cuts 40 arranged in the second pattern A2 have first depth "D" relative to the central longitudinal y-y axis and a second depth "C" relative to the central longitudinal y-y axis. In the depicted embodiment, the first depth D is larger than the second depth C. In other words, the cut 40 with depth D extends past the central longitudinal y-y axis, while the depth C extends short of the central longitudinal y-y axis.

With the depths D, C of the cuts 40 arranged in the second pattern A2, application of axial load on the cut portion 38 shown in FIG. 4, creates an unequal load across section e-e due to the cut patterns A1, A2. As such, the outer tube 28 begins to collapse toward the weaker side (i.e., the cuts 40 with depth D). The depths D, C of the cuts 40 can be adjusted to time the formation and shape of the outer tube 28 (as should be understood by a person of skill in the art in conjunction with a review of this disclosure). For example, the cuts 40 arranged in the first pattern A1 can extend well past the central longitudinal y-y axis, while the proceeding cuts 40, arranged in the second pattern A2, can extend closer to the central longitudinal y-y axis so that the cuts 40 arranged in the first pattern A1 will form before those arranged in the second pattern A2.

Figure 5:
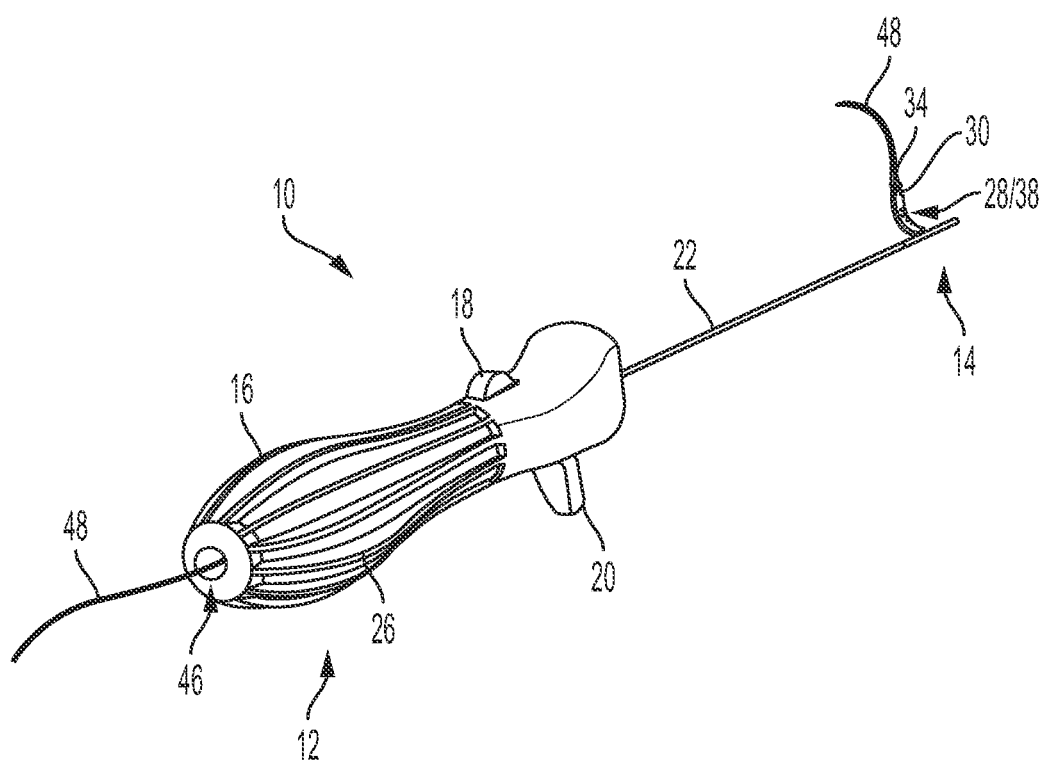
FIG. 5 is a back perspective view of a suture hook in a second configuration, according to an embodiment.
Figure 6:
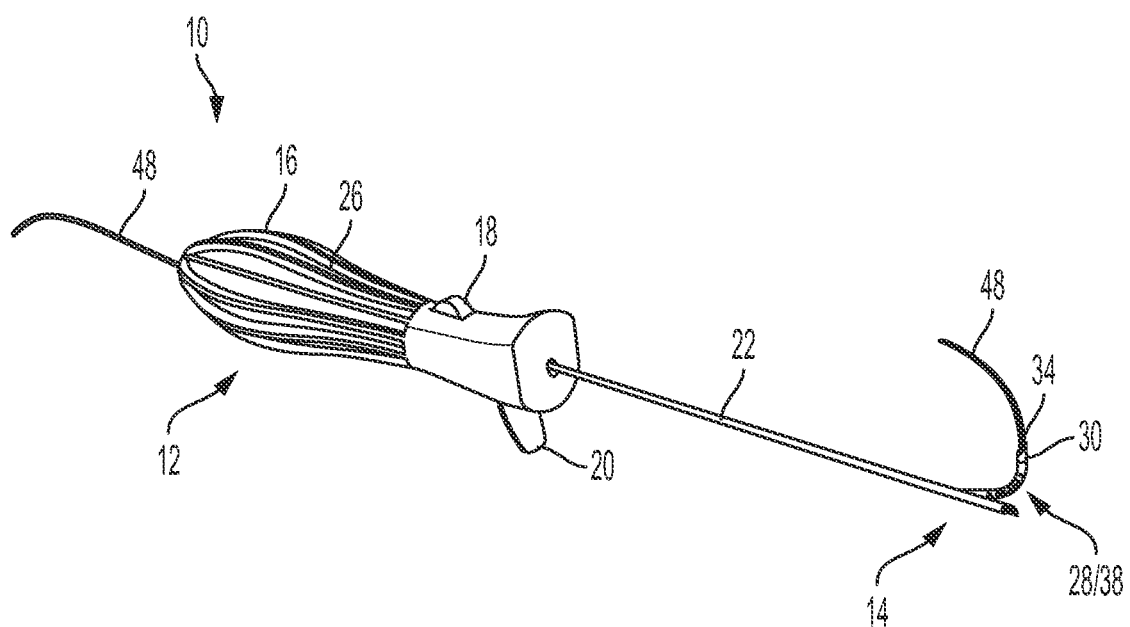
FIG. 6 is a front perspective view of the suture hook of FIG. 5.
Figure 7:
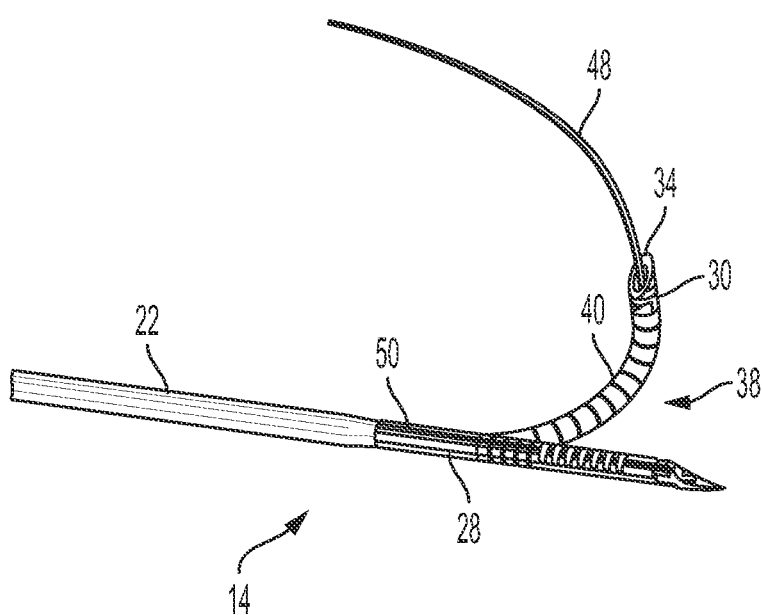
FIG. 7 is a close-up side perspective view of the distal end of the suture hook of FIG. 6.

Turning now to FIGS. 5-7, there are shown various views of the articulating suture hook 10 in the second configuration, according to an embodiment. FIG. 5 shows a back perspective view of a suture hook 10. The suture hook 10 of FIG. 5 comprises an inner channel 46 extending through the handle 16. The inner channel 46 of the handle 16 is in communication or otherwise extends to the inner channel (not shown) of the stiffening tube 22 and the inner channel 44 (FIG. 3) of the outer tube 28. The inner channel 46 extending through the handle 16 is sized and configured to pass or maintain a suture 48 therethrough. In the depicted embodiment, the suture 48 extends through the inner channel 46 in the handle 16 through the stiffening tube 22 and outer tube 28 and out from the distal tip 34 of the inner tube 30.

FIG. 6 shows a front perspective view of the suture hook 10 of FIG. 5. In use, traction is applied to the inner tube 30, which produces a compressive load against the end 32 of the outer tube 28. Traction is applied to the inner tube 30 by depressing the actuator 20. In the depicted embodiment, the actuator 20 is a ratcheting lever, as also shown in FIGS. 8-9, which pulls the inner tube 30 proximally when the ratcheting lever 20 is moved proximally. The force of the compressive load against the end 32 of the outer tube 28 (by the distal tip 34 of the inner tube 30) causes the flexible outer tube 28 to curve, bend, or otherwise deform to a second configuration, as shown in FIG. 6. Suture 48 is advanced through the stiffening tube 22, outer tube 28, and inner tube 30, and out through the distal tip 34 by actuating the suture advancing mechanism 18. In the depicted embodiment (and FIG. 9), the suture advancing mechanism 18 is a rotatable wheel (or linear slider, as should be understood by a person of ordinary skill in the art in conjunction with a review of this disclosure) extending at least partially within the handle 16, as shown in FIGS. 5-6. As the wheel 18 is rotated in the distal direction, it advances the suture 48 distally.

To transition the suture hook 10 from the second configuration back to the first configuration, pressure is applied to the inner tube 30. Pressure can be applied to the inner tube 30 by pushing on the inner tube 30, which causes the distal tip 34 to return to the first configuration (FIG. 1). In other words, to return to the first configuration, the traction is released by moving the actuator 20 in the opposing (distal) direction and the compressive load of the distal tip 34 of the inner tube 30 on the outer tube 28 is released. In another embodiment, to release the curvature of the outer tube 28 and move the outer tube 28 from the second configuration to the first configuration, the ratcheting lever 20 is displaced to the side, unlocking it from the ratchet. A spring assist returns the ratcheting lever 20 to a starting position and assists in pushing the inner tube 30 to straighten the outer tube 28 to the first configuration. In an alternative embodiment, as shown in FIG. 7 (and FIG. 2), a thin protective membrane 50 surrounds the cut portion 38 of the flexible cannulated outer tube 28 proximal to the shoulder 36 of the distal tip 34. The thin membrane 50 protects the cannula and/or surrounds soft tissue from the cuts 40 on the cut portion 38.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. An articulating suture hook, comprising:
    a handle having a proximal end and distal end;
    a stiffening tube fixed to the distal end of the handle and extending distally from the handle;
    a flexible outer tube comprising a body fixed to the stiffening tube and extending distally therefrom, wherein the flexible outer tube includes a first set of a plurality of cuts arranged in a first pattern, a second set of a plurality of cuts following the first set of the plurality of cuts arranged in a first pattern, wherein the plurality of cuts of the second set are integrally connected together by an elongated spine portion comprising an uncut portion of the outer tube body, and the second set is arranged in a second pattern similar to the first pattern, wherein the first pattern is axially offset from the second pattern wherein at least one cut of the plurality of cuts in the second set includes an open end, a first side interior surface connected at a bottom interior surface to a second side interior surface, wherein the side surfaces of the at least one cut of the plurality of cuts are further spaced apart at a first position proximate to the open end as compared to a position proximate to the bottom interior surface, and a portion of the elongated spine portion extends along a first axis adjacent to the bottom interior surface, and at least one cut opposite a cut of the plurality of cuts of the second set, wherein the at least one cut has a different sized open end as an open end of the cut of the plurality of cuts of the second set to which it is opposite;

wherein the cut of the plurality of cuts of the second set has a first depth and the at least one cut opposite the cut of the plurality of cuts of the second set has a second depth relative to a central longitudinal axis, wherein the central longitudinal axis is different from and parallel to the first axis and extends through the flexible outer tube;

wherein the first depth extends past the central longitudinal axis and the second depth is short of the central longitudinal axis;

wherein in a first configuration, the flexible outer tube extends parallel to or in alignment with the stiffening tube; and wherein in a second configuration, the flexible outer tube is curved at the cut portion.

2. The suture hook of claim 1, wherein the first set is offset by an angle of 90 degrees from the second set.

3. The suture hook of claim 1, wherein the first depth is larger than the second depth.

4. The suture hook of claim 1, wherein the outer tube is connected to a sharp distal tip.

5. An articulating suture hook, comprising:
a cannulated handle having a proximal end and distal end;
a cannulated stiffening tube fixed to the distal end of the handle and extending distally from the handle;
a flexible cannulated outer tube comprising a body fixed to the stiffening tube and extending distally therefrom;
a flexible cannulated inner tube slidably attached to the flexible cannulated outer tube, the flexible cannulated inner tube having a distal tip;
a plurality of cuts positioned along a cut portion of the flexible outer tube;
a first set of the plurality of cuts arranged in a first pattern;
a second set of the plurality of cuts following the first set of the plurality of cuts arranged in a first pattern, wherein the plurality of cuts of the second set are integrally connected together by an elongated spine portion comprising an uncut portion of the outer tube body, and the second set is arranged in a second pattern similar to the first pattern, wherein the first pattern is axially offset from the second pattern, wherein at least one cut of the plurality of cuts in the second set includes an open end, a first side interior surface connected at a bottom interior surface to a second side interior surface, wherein the side surfaces of the at least one cut of the plurality of cuts are further spaced apart at a first position proximate to the open end as compared to a position proximate to the bottom interior surface, and a portion of the elongated spine portion extends along an axis adjacent to the bottom interior surface, and at least one cut opposite a cut of the plurality of cuts of the second set, wherein the at least one cut has a different sized open end as an open end of the cut of the plurality of cuts of the second set to which it is opposite;

wherein the cut of the plurality of cuts of the second set has a first depth and the at least one cut opposite the cut of the plurality of cuts of the second set has a second depth relative to a central longitudinal axis, wherein the central longitudinal axis is different from and parallel to the first axis and extends through the flexible outer tube;

wherein the first depth extends past the central longitudinal axis and the second depth is short of the central longitudinal axis;

wherein in a first configuration, the flexible cannulated outer tube extends parallel to or in alignment with the cannulated stiffening tube; and wherein in a second configuration, the flexible cannulated outer tube is curved at the cut portion.

6. The suture hook of claim 5, wherein each cut of the first set is offset by an angle from each cut of the second set.

7. The suture hook of claim 6, wherein the angle is 90 degrees.

8. The suture hook of claim 5, wherein the first depth is larger than the second depth.

9. The suture hook of claim 5, further comprising a ratcheting lever operably attached to the handle and the flexible cannulated inner tube, such that actuating the ratcheting lever proximally applies traction to the flexible cannulated inner tube.

10. The suture hook of claim 9, wherein traction of the inner tube on the outer tube causes the outer tube to move from the first configuration to the second configuration.

11. The suture hook of claim 5, further comprising a suture extending through the handle, the flexible cannulated outer tube, and flexible cannulated inner tube, and extending distally out from the distal tip.

12. The suture hook of claim 11, further comprising a suture advancing mechanism operably attached to the handle, such that actuation of the suture advancing mechanism moves the suture through the handle and distally out of the distal tip.

13. The suture hook of claim 5, further comprising a protective membrane surrounding the cut portion of the flexible cannulated outer tube.

14. The suture hook of claim 5, further comprising grooves positioned along at least a portion of the handle.

* * * * *